United States Patent
Suzuki et al.

[11] Patent Number: 6,015,275
[45] Date of Patent: Jan. 18, 2000

[54] MAGNETICALLY SUSPENDED CENTRIFUGAL PUMP APPARATUS WITH AN AUTOMATIC NEUTRAL POSITION SETTING CONTROL

[75] Inventors: Minoru Suzuki, Shizuoka; Toshihiko Nojiri, Kanagawa, both of Japan

[73] Assignee: NTN Corporation, Osaka, Japan

[21] Appl. No.: 08/991,877

[22] Filed: Dec. 16, 1997

[30] Foreign Application Priority Data

Dec. 26, 1996 [JP] Japan .................................. 8-347369

[51] Int. Cl.[7] ........................ F04B 17/00; H02K 7/09
[52] U.S. Cl. ........................ 417/423.12; 310/90.5
[58] Field of Search ................ 417/423.12, 420; 310/90, 90.5, 68 R; 415/118, 900

[56] References Cited

U.S. PATENT DOCUMENTS

| | | | |
|---|---|---|---|
| 4,642,500 | 2/1987 | Higuchi et al. | 310/90.5 |
| 4,683,391 | 7/1987 | Higuchi | 310/90.5 |
| 5,302,874 | 4/1994 | Pinkerton | 310/90.5 |
| 5,350,283 | 9/1994 | Nakazeki et al. | 417/423.7 |
| 5,576,587 | 11/1996 | Takahashi et al. | 310/90.5 |
| 5,666,014 | 9/1997 | Chen | 310/90.5 |
| 5,772,564 | 6/1998 | Taniguchi et al. | 483/7 |
| 5,777,414 | 7/1998 | Conrad | 310/90.5 |
| 5,783,885 | 7/1998 | Post | 310/90.5 |
| 5,798,454 | 8/1998 | Nakazeki et al. | 73/54.28 |
| 5,911,558 | 6/1999 | Nakazeki et al. | 415/118 |

*Primary Examiner*—Charles G. Freay
*Assistant Examiner*—Robert Z. Evora
*Attorney, Agent, or Firm*—McDermott, Will & Emery

[57] ABSTRACT

In order to enable speedy and simple exchanging operation of impeller and casing by eliminating setting operation, a sensor output when the impeller is not floating is measured by an automatic neutral position setting circuit at the activation of an electromagnet as an active magnetic bearing, the sensor output is compared with a predetermined set value and difference therebetween is calculated, which difference is used for adjusting the sensor output.

5 Claims, 5 Drawing Sheets

MAGNETICALLY SUSPENDED CENTRIFUGAL PUMP APPARATUS WITH AN AUTOMATIC NEUTRAL POSITION SETTING CONTROL

BACKGROUND OF THE INVENTION

FIELD OF THE INVENTION

The present invention relates to a magnetically suspended centrifugal pump apparatus. More specifically, the present invention relates to a magnetically suspended centrifugal pump apparatus used for a medical equipment such as a blood pump, an artificial heart-lung and an artificial heart.

FIGS. 3A to 3C show cross sectional structure of a magnetically suspended centrifugal blood pump, in which FIG. 3B is a cross section taken along the line A—A of FIG. 3A and FIG. 3C is taken along the line B—B of FIG. 3A. The blood pump shown in FIG. 3A includes, as four main components, a magnetic bearing 1, a casing 2, an impeller 3 and a motor 4. As impeller 3 rotates, blood enters a central inlet port 5 of magnetic bearing 1, is pumped in casing 2, and discharged from an outlet port 6.

Impeller 3 includes, as shown in FIG. 4, permanent magnets 8 arranged spaced by an equal distance from each other circumferentially, and a ferromagnetic disc 9, provided on opposing sides of a vane 7. Impeller 3 floats in casing 2 on the balance between attractions on internal permanent magnets 8 and permanent magnets 10 arranged opposing thereto, or attractions between ferromagnetic disc 9 of impeller 3 on the opposite side and a plurality of magnetic bearings 1. At this time, impeller 3 is actively controlled by magnetic bearing 1. Control in the radial direction and driving for rotation are performed by a magnetic coupling provided by permanent magnets 8 and 10. Magnetic bearing 1 includes electromagnets 11 and a sensor 12. By calculating an output from sensor 12, current in each electromagnet 11 is controlled.

FIG. 5 shows a magnetic bearing control apparatus with respect to one axis only, in which movement in the directions of two axes, that is, $\theta_x$ and $\theta_y$ are not considered but only the movement and its control along the z axis are represented, facilitating understanding of the operation of magnetic bearing 1. Referring to FIG. 5, when control circuit 16 is in operation, position of impeller 3 is measured by a sensor 12, a signal is passed to electromagnet 11 through sensor amplifier 18, control circuit 16 and amplifier 17. In this manner, impeller 3 is controlled such that it floats at a prescribed position in casing 2, dependent on the balance between attraction of electromagnets 11 and attraction of magnetic coupling. The prescribed position is determined by a neutral position setting operation in advance, such that the position is at the center of casing 2 (where spaces between opposing surfaces of impeller 3 and housing are A=B), by adjusting sensor amplifier 18.

FIGS. 6 to 8 are illustrations showing the neutral position setting operation. In the neutral position setting operation, as a preparation, motor 4 shown in FIG. 5 is removed so that external force is not applied to impeller 3, as shown in FIG. 6, and current of electromagnets 11 are not provided. Direction and amount of movement of impeller 3 are represented by polarity and voltage of an output of sensor amplifier 18 from the neutral position. For this purpose, a spacer 23 having the thickness A which is the same as the space A at the end surface when impeller 3 is at the neutral position is placed between magnetic bearing 1 and impeller 3, so that impeller 3 is positioned at the neutral position, the output from sensor amplifier 18 at this time is set to 0 [v], and offset is adjusted.

Thereafter, referring to FIG. 7, in order to set an output gain with respect to the amount of movement, spacer 23 is removed, magnetic bearing 1 and impeller 3 are brought into tight contact, an output at that time is set to a predetermined voltage X [v], and the sensor gain is adjusted. As a result, when motor 4 removed from adjustment is again attached to casing 2 as shown in FIG. 8, impeller 3 would be brought into tight contact with that end surface of the casing which faces the magnetic coupling because of attraction by the magnetic coupling, when electromagnets 11 are not controlled. The output from sensor amplifier 18 is –X [v] at this time, since impeller 3 is at the same distance A in the opposite direction from the neutral position.

As described above, sensor offset adjustment is necessary when the impeller is exchanged, because of variations of ferromagnetic disc 9 used in impeller 3, as shown in FIG. 4. As a result, in a blood pump for open heart surgery in which impeller 3 is an article of consumption, it becomes necessary to perform the above described neutral position setting operation every time impeller 3 is exchanged, which requires labor for exchanging operation and skill for setting operation.

SUMMARY OF THE INVENTION

Therefore, an object of the present invention is to provide a magnetically suspended centrifugal pump apparatus which allows speedy and simplified exchange of impeller and casing, by eliminating setting operation at the time of exchange.

Briefly stated, the magnetically suspended centrifugal pump apparatus in accordance with the present invention includes a housing having a blood inlet port and a blood outlet port in which an impeller rotates, a centrifugal blood pump for feeding blood by centrifugal force caused by rotation of the impeller, a passive magnetic bearing for controlling position of the impeller, and an active magnetic bearing including an electromagnet and a position sensor for detecting position of the impeller, in which the impeller rotates held at a prescribed position in the housing by the function of passive and active magnetic bearings, and the apparatus further includes a neutral position setting circuit for measuring an output from the position sensor when the impeller is not floating at activation of the active magnetic bearing, comparing the output of the position sensor with a predetermined measured value and calculating difference therebetween, and adjusting the output of the position sensor by using the calculated difference.

Therefore, according to the present invention, the output from the position sensor when the impeller is not floating is measured before the activation of the active magnetic bearing, the output is compared with a predetermined set value and difference therebetween is calculated, which difference is used for adjusting the sensor output. Accordingly, setting operation at the time of exchange of the impeller and the casing can be eliminated, which results in speedy and simplified exchanging operation.

In a preferred embodiment of the present invention, the automatic neutral position setting circuit includes an A/D converting circuit for converting the sensor output to a digital signal, an operating circuit for calculating difference between the output from the A/D converting circuit and a reference output of the sensor, and a D/A converting circuit for converting an output signal from the operating circuit to an analog signal. More preferably, there is provided a latch circuit for latching the difference calculated by the operating circuit.

More preferably, in order to control conduction to the electromagnet current of the active magnetic bearing during measurement of automatic neutral position setting circuit, there is provided a switch of which on/off is controlled by a signal from the automatic neutral position setting circuit. Further, a control signal provided from the operating circuit to control the switch is latched by a flipflop.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
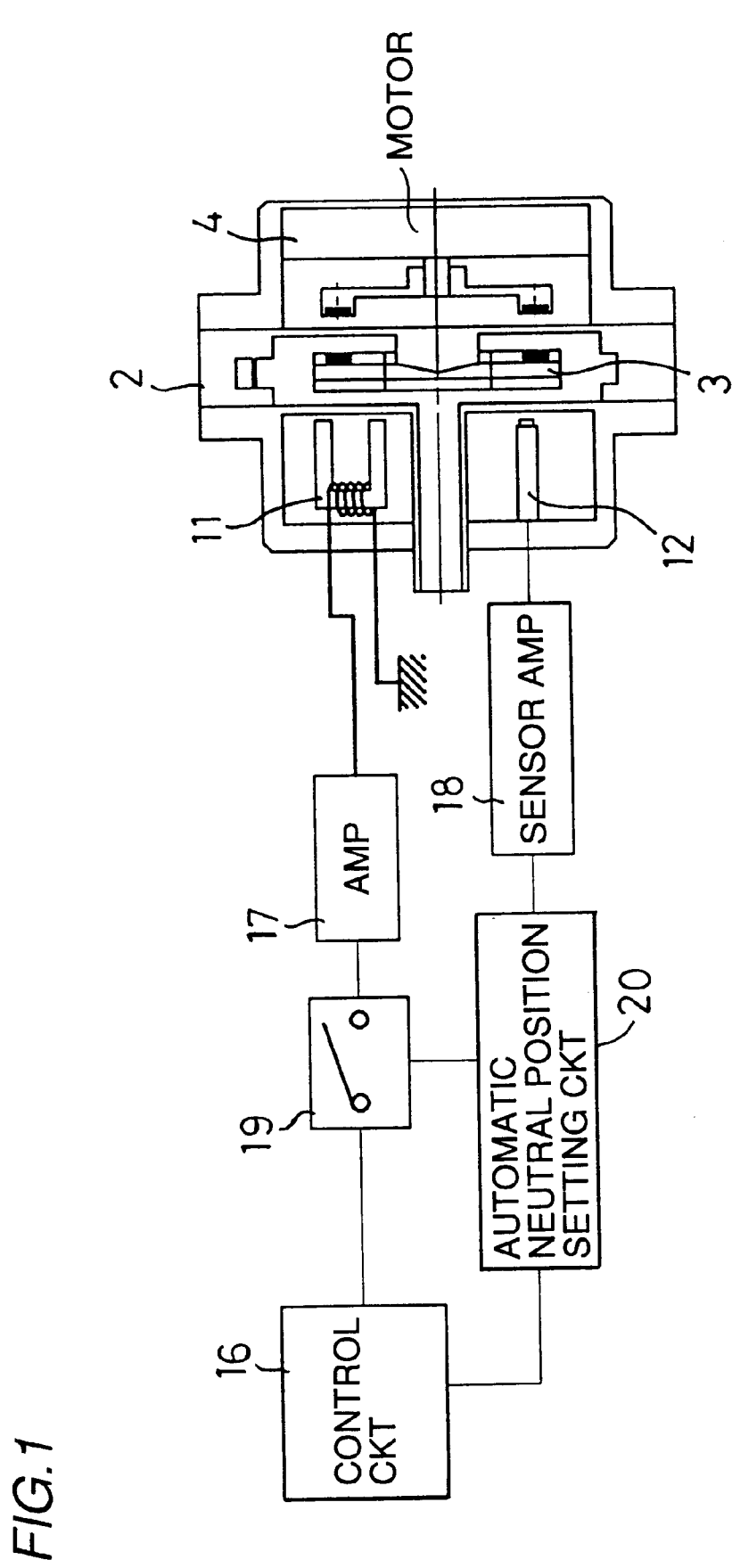
FIG. 1 shows one embodiment of the present invention.
Figure 5:
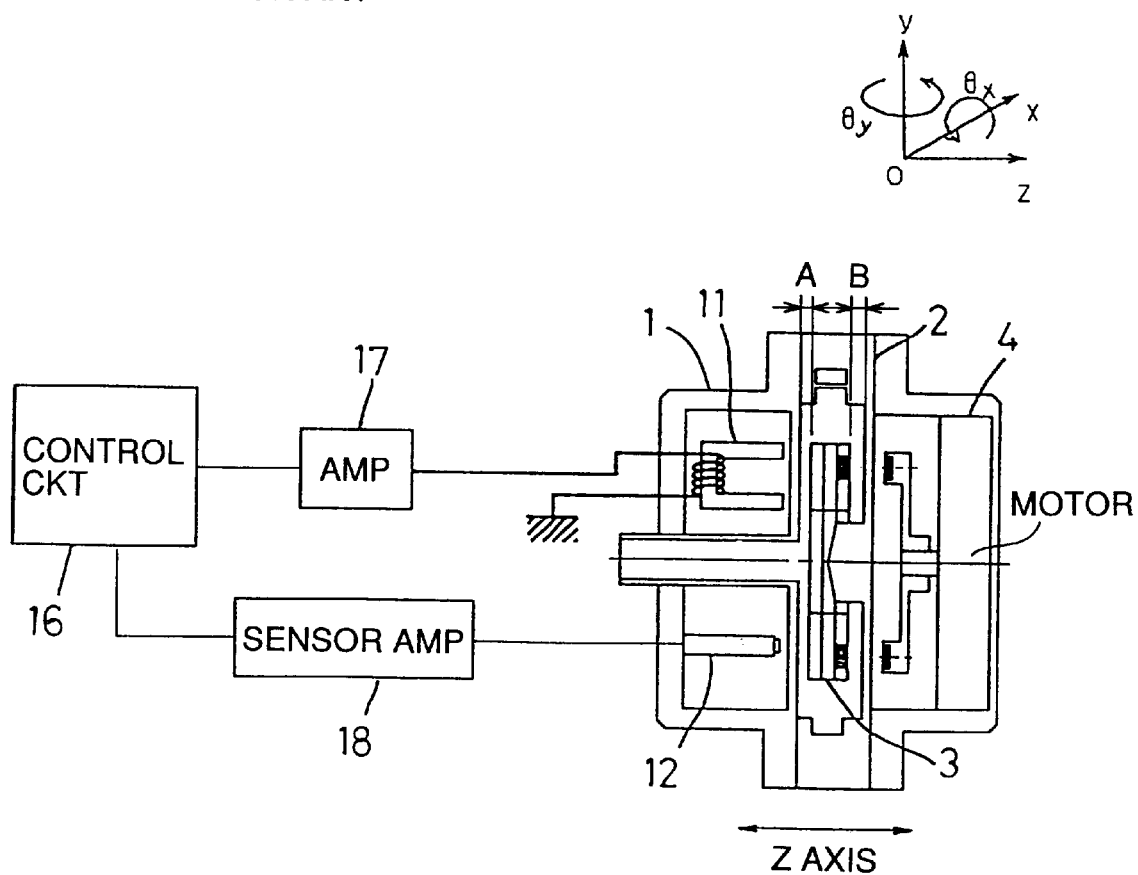
FIG. 5 shows the magnetic bearing control apparatus goalong one axis, in which movement in the directions of two axes, that is, $\theta_x$ and $\theta_y$ are not considered, representing movement and control only along the z axis, for facilitating understanding of the operation of the magnetic bearing shown in FIG. 3.
Figure 6:
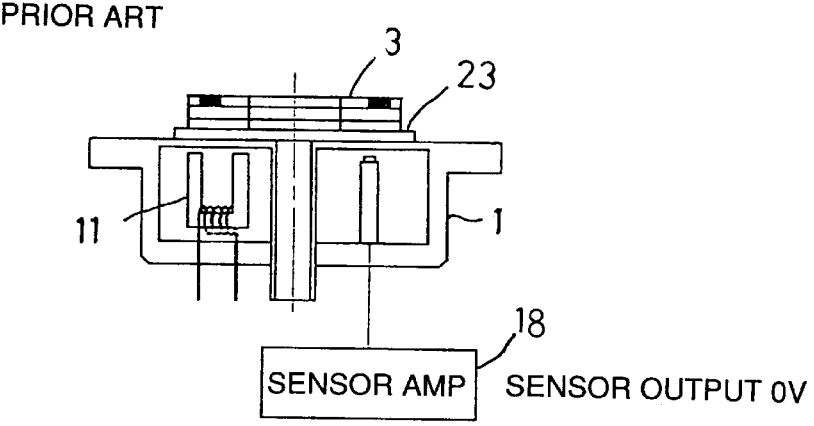
FIG. 6 is an illustration related to a method of adjustment of impeller at the neutral position.
Figure 7:
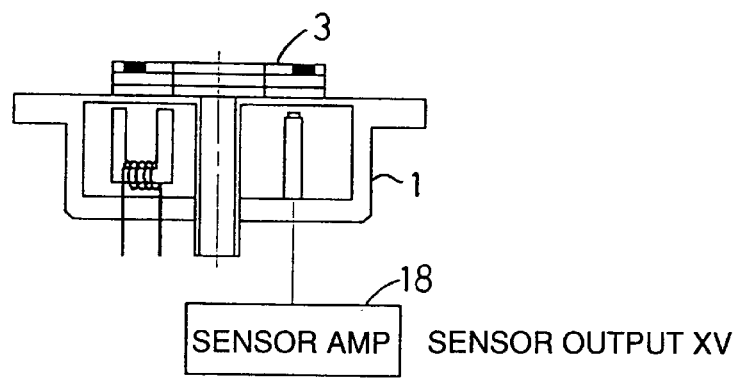
FIG. 7 is an illustration showing sensor gain adjustment.

FIG. 1 shows an embodiment of the present invention. In the embodiment shown in FIG. 1, an automatic neutral position setting circuit 20 is provided between control circuit 16 and sensor amplifier 18 shown in FIG. 5, and a switch 19 is provided between control circuit 16 and amplifier 17. Automatic neutral position setting circuit 20 is provided for measuring the output from the position sensor when impeller 3 is not floating before the activation of active magnetic bearing, comparing the sensor output with a predetermined measured value and calculating the difference therebetween, for adjusting the sensor output using the calculated difference.

Figure 2:
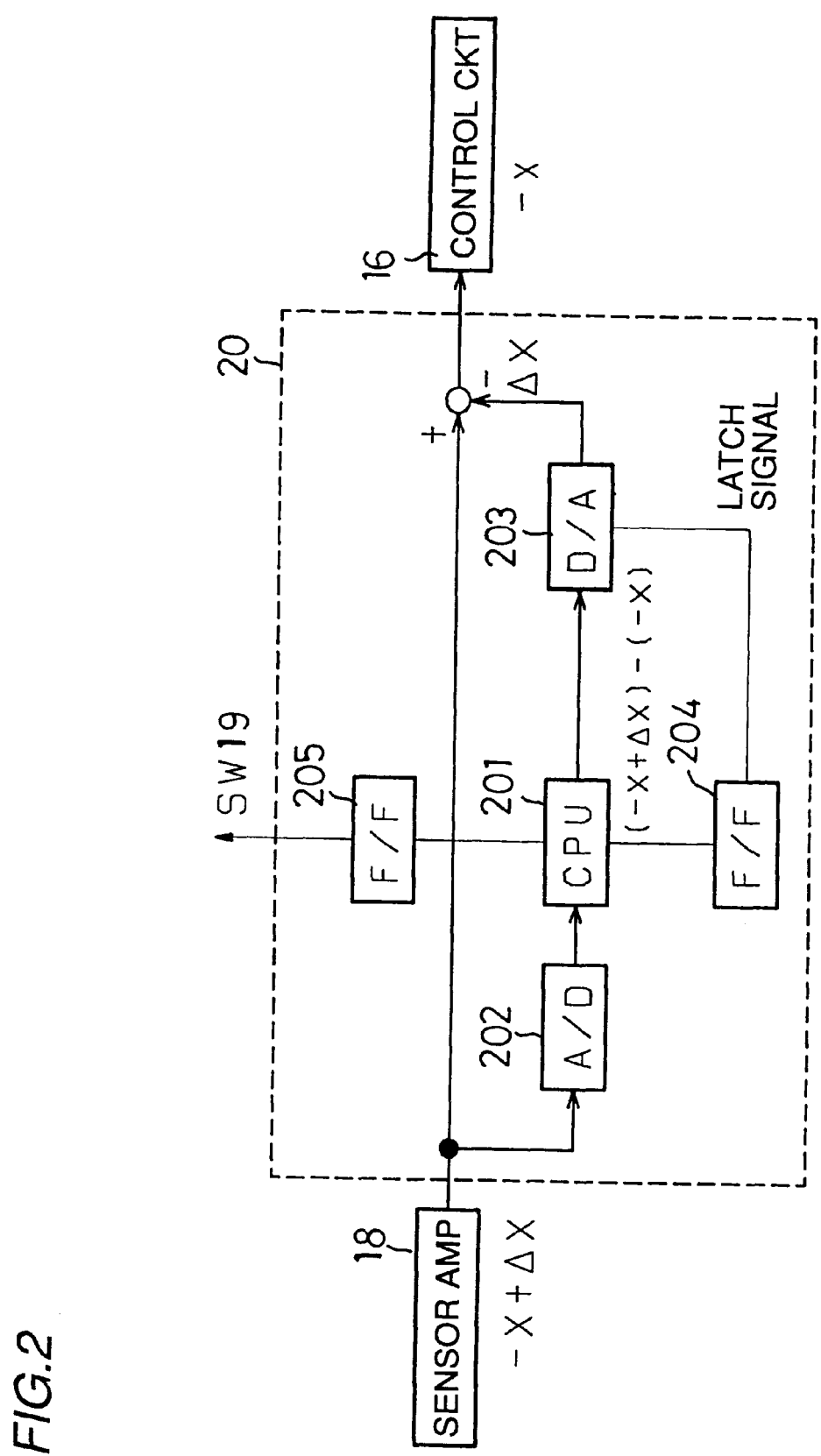
FIG. 2 is a specific block diagram of the automatic neutral position setting circuit shown in FIG. 1.
Figure 3C:
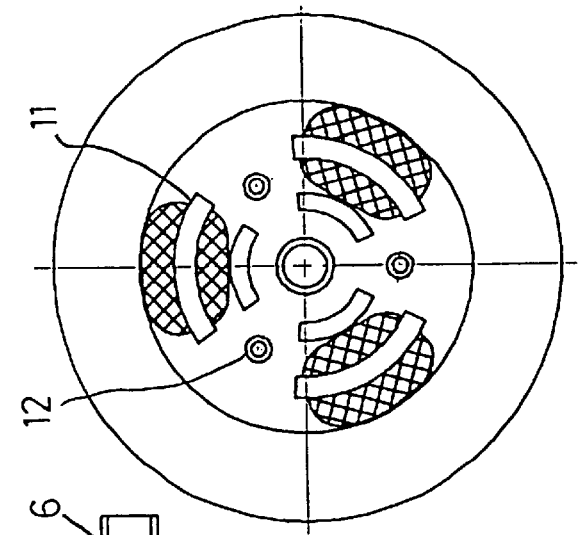
FIGS. 3A to 3C are cross sections of the magnetically suspended centrifugal blood pump.
Figure 3B:
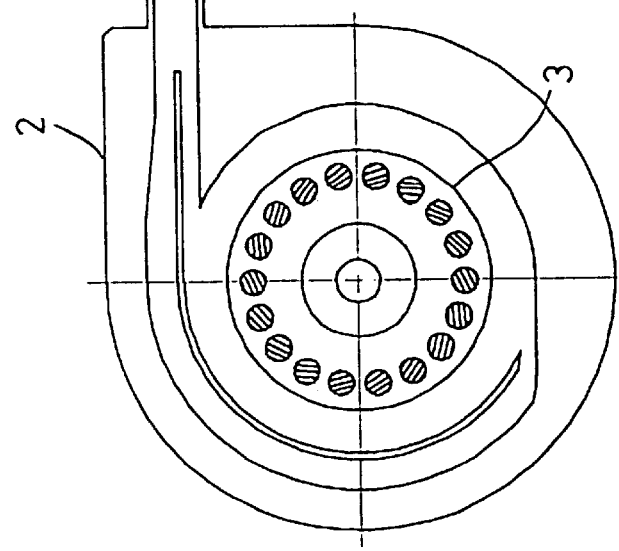
Figure 3A:
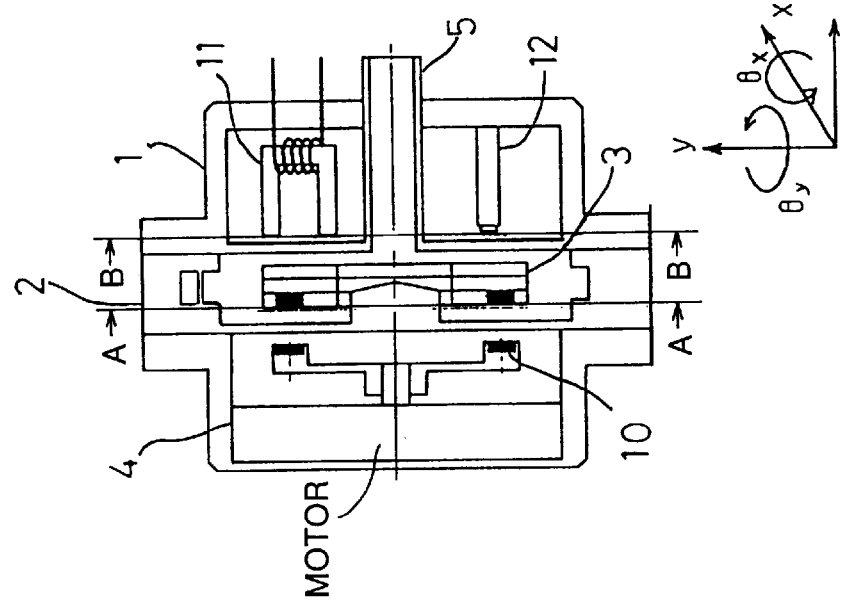
Figure 4:
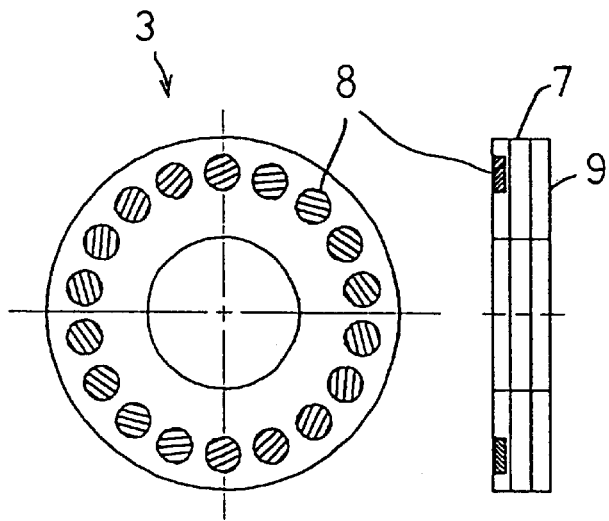
FIG. 4 shows the impeller of FIGS. 3A to 3C.

FIG. 2 is a specific block diagram of automatic neutral position setting circuit 20 shown in FIG. 1. Automatic neutral position setting circuit 20 includes, as shown in FIG. 2, a CPU 201, an A/D converter 202, a D/A converter 203 and flipflops 204 and 205. An output from sensor amplifier 18 is applied to A/D converter 202, turned to a digital signal, and applied to CPU 201. CPU 201 performs a prescribed operation on the sensor output, and applies the result of operation to D/A converter 203 where the result is turned to an analog signal, which analog signal is subtracted from the original output of the sensor amplifier 18. The switch connected between control circuit 16 and amplifier 17 shown in FIG. 1 is turned on/off by a latch signal applied from CPU 201 through flipflop 205, enabling selection of connection/disconnection of the signal from control circuit 16 to amplifier 17.

Figure 8:
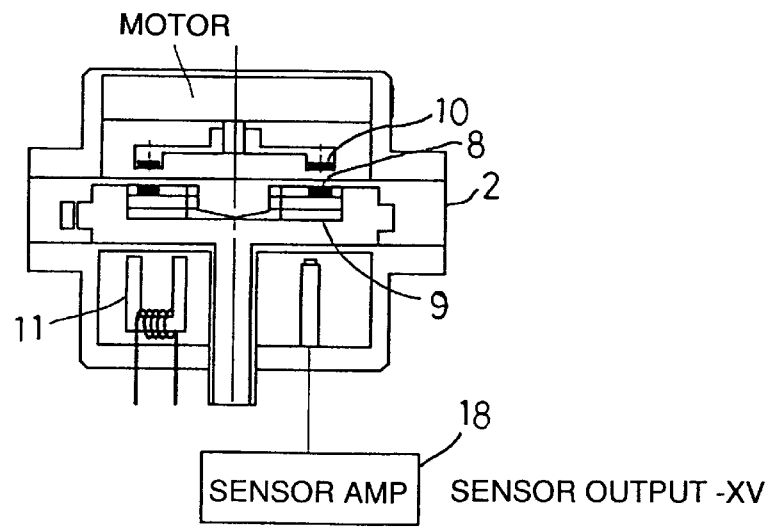
FIG. 8 shows a state how the sensor output −X [v] is output from the sensor amplifier after offset adjustment.

Specific operation of one embodiment of the present invention will be described in the following. It is assumed that at the first activation of the apparatus, neutral position is set (offset and gain are adjusted) in accordance with the conventional method once and the invention is utilized from the next and the following exchange of the impeller and the casing. As shown in FIG. 8, when the current of electromagnetic 11 is not provided, impeller 3 is in tight contact with that end surface which faces the motor, by the attraction of magnetic coupling provided by permanent magnets 10 and 8. In this case, the output from sensor amplifier 18 should indicate −X [v]. However, when the impeller 3 is exchanged to a new one, the output may possibly be −X+Δx[v], because of variation of individual impeller 3. In such a case, if the setting is maintained as it is, the neutral position would be offset by the amount corresponding to Δx[v]. Therefore, the output from sensor amplifier 18 is applied as an input to neutral position setting circuit 20.

The output from sensor amplifier 18 is turned to a digital signal by A/D converter 202, and by CPU 201, difference Δx[v] from the reference value −X[v] is calculated. Further, the output from CPU 201 is turned to an analog signal by D/A converter 203, and the difference Δx[v] is subtracted from the output −X+Δx[v] of sensor amplifier 18. As a result, the output of sensor amplifier 18 can be adjusted to −X[v], and offset Δx[v] of the output signal from sensor amplifier 18 applied to control circuit 16 can be eliminated. As a result, the original neutral position is ensured regardless of the variation of the impellers.

It is necessary that the value Δx[v] obtained through measurement is set at the activation of the apparatus and that the value is held thereafter as long as the apparatus is being driven. For this purpose, a latch signal is applied from CPU 201 to the latch circuit of D/A converter 203 so as to hold the analog signal output from D/A converter 203. However, if CPU 201 should run away because of noise or the like during the operation of the pump, the latch signal would not be ensured, disabling normal operation of the pump. Therefore, latch circuit is formed with a flipflop circuit 204 inserted, rather than direct latching of D/A converter 203 by CPU 201. Accordingly, even if CPU 201 should run away after the neutral position is set, the latch signal of D/A converter 203 is maintained unless flipflop circuit 204 is reset, and therefore the analog signal output is ensured. Further, flipflop circuit 205 has similar function of latching the signal from CPU 201 to switch 19 for connecting/disconnecting the signal from control circuit 16 to amplifier 17.

As described above, according to the present invention, the output of position sensor when the impeller is not floating is measured before the activation of the active magnetic bearing, the sensor output is compared with a predetermined set value and the difference therebetween is calculated, which difference is used for adjusting the sensor output. Therefore, the operation of setting can be eliminated at the time of exchanged of the impeller and the casing, whereby speedy and simplified exchanging operation becomes possible.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A magnetically suspended centrifugal pump apparatus, comprising:

a housing having a blood inlet port and a blood outlet port;

a centrifugal blood pump having an impeller rotating in said housing and feeding blood by centrifugal force caused by rotation;

a passive magnetic bearing for controlling position of said impeller; and an active magnetic bearing including a position sensor for detecting the position of said impeller, and an electromagnet; wherein said impeller rotates maintained at a prescribed position in said housing by function of said passive and active magnetic bearings;

said apparatus further comprising automatic neutral position setting means for measuring an output of said sensor when said impeller is not floating before activation of said active magnetic bearing, comparing the output of said sensor with a predetermined measured value and calculating difference therebetween, for adjusting said sensor output.

2. The magnetically suspended centrifugal pump apparatus according to claim 1, wherein said automatic neutral position setting circuit includes A/D converting means for converting said sensor output to a digital signal, operating means for calculating difference between an output of said A/D converting means and a reference output of said sensor, and D/A converting means for converting an output signal from said operating means to an analog signal.

3. The magnetically suspended centrifugal pump apparatus according to claim 2, wherein said automatic neutral position setting means includes latch means for latching the difference calculated by said operating means.

4. The magnetically suspended centrifugal pump apparatus according to claim 1, further comprising a switch of which on/off is controlled by a signal from said automatic neutral position setting means, for controlling current to an electromagnet in said active magnetic bearing during measurement by said automatic neutral position setting means.

5. The magnetically suspended centrifugal pump apparatus according to claim 4, further comprising a flipflop for latching a control signal output from said operating means for controlling said switch.

* * * * *